United States Patent
Lindner et al.

(10) Patent No.: US 6,228,382 B1
(45) Date of Patent: May 8, 2001

(54) MICROBIOCIDAL MIXTURES

(75) Inventors: Wolfgang Lindner, Seelze; Jörg Rothermel, Freigericht, both of (DE)

(73) Assignee: ETC C.V., Hamilton (BM)

( * ) Notice: Subject to any disclaimer, the term of this patent is extended or adjusted under 35 U.S.C. 154(b) by 0 days.

(21) Appl. No.: 09/319,706

(22) PCT Filed: Dec. 9, 1997

(86) PCT No.: PCT/EP97/06871

§ 371 Date: Jun. 9, 1999

§ 102(e) Date: Jun. 9, 1999

(87) PCT Pub. No.: WO98/25464

PCT Pub. Date: Jun. 18, 1998

(30) Foreign Application Priority Data

Dec. 10, 1996 (DE) .............................................. 196 51 351

(51) Int. Cl.[7] .................................................... A01N 43/80
(52) U.S. Cl. .......................... 424/405; 514/241; 514/245; 514/372
(58) Field of Search ............................ 424/405; 514/372, 514/241, 245

(56) References Cited

U.S. PATENT DOCUMENTS

| | | | |
|---|---|---|---|
| 3,452,034 | * 6/1969 | Tomcufcik et al. ................. | 548/137 |
| 3,523,121 | * 8/1970 | Lewis et al. .......................... | 548/213 |
| 3,761,488 | * 9/1973 | Lewis et al. .......................... | 548/213 |
| 4,105,431 | * 8/1978 | Lewis et al. .......................... | 504/156 |
| 4,243,403 | * 1/1981 | Lewis et al. .......................... | 504/156 |
| 4,265,899 | * 5/1981 | Lewis et al. .......................... | 514/372 |
| 4,279,762 | * 7/1981 | Lewis et al. .......................... | 508/271 |
| 4,322,475 | * 3/1982 | Lewis et al. .......................... | 428/497 |
| 4,325,201 | * 4/1982 | Lewis et al. .......................... | 504/100 |
| 5,125,967 | * 6/1992 | Morpeth et al. ................... | 106/18.22 |
| 5,466,382 | * 11/1995 | Downey et al. ...................... | 210/764 |
| 5,853,463 | * 12/1998 | Willingham et al. .............. | 106/18.35 |

* cited by examiner

Primary Examiner—Robert H. Harrison
(74) Attorney, Agent, or Firm—Robert F. Tavares

(57) ABSTRACT

Mixture comprising as active substance
- a) 0.01 to 99.99% by weight of at least one 2-alkylisothiazolin-3-one or at least one derivative thereof or a mixture of at least one 2-alkylisothiazolin-3-one and at least one derivative thereof and
- b) 0.01 to 99.99% by weight of at least one other, microbicidally active compound where the sum of a) and b) is 100% by weight of the active substance of the mixture, characterized in that the at least one 2-alkylisothiazolin-3-one or the at least one derivative thereof has an octanol/water partition coefficient (logPow) of from 3 to 5.

20 Claims, No Drawings

MICROBIOCIDAL MIXTURES

Coated synthetic or natural materials which are exposed to the weather are quickly colonized by microorganisms (microbes), such as bacteria, mould fungi, yeasts, lichen or algae and damaged by the products of their metabolism. Thus, plasters, for example on insulating layers such as polystyrene panels (integral thermal insulation systems), on exterior facades or in damp locations, such as, for example, swimming pools, quickly change their colour to from green to black, owing to colonization by algae.

When preparing such coating materials, it is therefore customary to add biocides, for example microbiocidaly active substances, i.e. substances which substantially prevent the growth of microorganisms, or biostatics, such as, for example, microbiostatic substances, i.e. substances which only inhibit the growth of microorganisms, to extend the life of said coating materials and, in particular, to ensure a long-lasting high optical quality of the coatings.

Likewise, objects, such as, for example, leather, paper, such as, for example, cardboard boxes, plastics and the like are, when they are in the open and exposed to the action of weather, or when they are used or stored in damp locations, subject to colonization by microorganisms. Such a colonization can not only have a negative effect on the use properties of the abovementioned objects; in general, the optical appeal is affected to a considerably greater extent, a fact which in most cases constitutes a loss in value for the owner of the object in question.

Suitable microbiocides for the microbiocidal finishing of the abovementioned objects and coating materials are, for example, tributyltin compounds, 2-n-octylisothiazoli-none, carbendazim, 2-thiocyanatomethylthiobenzothiazole, terbutryn or diuron.

However, it has been found that the substances which have hitherto been used for microbiocidal finishing cannot ensure a long-lasting protection against colonization. Most of the microbicides known from the prior art are, under the influence of moisture, leached out from the objects which are finished with them. This results in a continuous decrease of the microbiocidaly active compound in the object in question, whose protection against colonization by microbes therefore approaches zero within a longer or shorter period of time (depending on the exposure to moisture). Another associated disadvantageous aspect is the high discharge of the microbiocides into the environment.

Microbiocides which are frequently used in practice include the isothiazolin-3-ones which are substituted in the 2-position, in particular 2-n-octylisothiazolin-3-one. It is employed for a number of substances and objects which are, for example during use and storage outdoors or in damp locations, subject to colonization by microbes, such as, for example, algae, lichen, fungi and the like. One use example is paint for facades.

The patents U.S. Pat. No. 3,523,121, U.S. Pat. No. 3,761,488 and U.S. Pat. No. 4,243,403 describe the preparation and the microbicidal properties of 2-alkylisothiazolinones including, inter alia, 2-n-octyl-, 2-n-nonyl- and 2-n-decylisothiazolin-3-one. However, in these publications, no statements are made concerning the leaching behaviour of the compounds and their combination with other biocides, in particular microbiocides.

The compounds which have hitherto been used as microbiocides often, when used on their own, have an incomplete activity spectrum. In practice, use is therefore frequently made of combinations of a plurality of microbiocides, to achieve an activity spectrum that is as wide and as comprehensive as possible.

Products which, in addition to 2-n-octylisothiazolin-3-one, comprise other fungicidally and algicidally active compounds (for example MERGAL® S 89 paste and MERGAL® S 90 paste) are commercially available.

However, here it is disadvantageous that, in general, some of the 2-n-octylisothiazolin-3-one is leached out under the influence of moisture (for example, in the case of outdoor applications) from the object that has been finished with it, and is thus withdrawn from the active compound combination. This results in a "gap" in the microbiocidal protection, and colonization by corresponding microbes may occur.

It was therefore the object to provide microbiocides which meet the following requirements:

a) a microbiocidal activity spectrum which is as wide as possible, where the fungicidal activity should, if possible, also cover fungi which are particularly resistant towards fungicides, such as, for example, fungi of the order Alternaria, Mucor or Ulocladium, or yeasts, b) have a low tendency for leaching out from the microbiocidaly finished objects and substances.

The object was, in particular, to provide a replacement for 2-n-octylisothiazolin-3-one in microbiocidal mixtures which has a comparable microbiocidal activity but which is leached out to a lesser extent.

Surprisingly, it has now been found that mixtures of 2-alkylisothiazolin-3-ones which have an octanol/water partition coefficient (logPow) of from 3 to 5 and other microbiocidal compounds exhibit a long-lasting activity against microorganisms in objects finished with them. Furthermore, the abovementioned mixtures have a wide activity spectrum against microorganisms and offer comprehensive protection against colonization by yeasts, fungi, algae and lichen.

Furthermore, it has surprisingly been found that the 2-alkylisothiazolin-3-ones in a mixture with one or more algicides are suitable for incorporation into materials such as, for example, plastic, leather, paper, wood, a sealant or a coating material, both water-based and solvent-based, and that they exert a long-lasting microbiocidal effect therein.

Furthermore, it has surprisingly been found that the known fungicidal activity of the 2-alkylisothiazolin-3-ones also covers fungi such as, for example, Alternaria, Mucor or Ulocladium which are very resistant towards fungicides and also yeasts which may grow in particular in food-processing plants, for example on wall coatings which have been finished with conventional fungicides.

The invention therefore provides a mixture comprising as active substance a) 0.01 to 99.99% by weight of at least one 2-alkylisothiazolin-3-one or at least one derivative thereof or a mixture of at least one 2-alkylisothiazolin-3-one and at least one derivative thereof and b) 0.01 to 99.99% by weight of at least one other, microbiocidaly active compound where the sum of a) and b) is 100% by weight of the active substance of the mixture, characterized in that the at least one 2-alkylisothiazolin-3-one or the at least one derivative thereof has an octanol/water partition coefficient (logPow) of from 3 to 5.

For the purpose of the invention, "active substances" are those substances present in the mixture which show microbiocidal activity.

For the purpose of the invention, "derivatives" are compounds whose chemical skeleton (i.e. the moiety responsible for the basic generic activity of the compound) is identical with that of the originally defined compound, but which have been chemically modified to improve, adapt or change a biological, chemical or physical property in another way. Accordingly, a derivative of a 2-alkylisothiazolin-3-one, for example, may be a 2-alkylisothiazolin-3-one which is substituted in the 4-position by a halogen. Further derivatives of the 2-alkylisothiazolin-3-one are mentioned in the patents U.S. Pat. No. 3,523,121, U.S. Pat. No. 3,761,488 and U.S. Pat. No. 4,243,403.

The term "octanol/water partition coefficient" denotes the logarithm to base ten of the partition coefficient between n-octanol and water.

The mixture according to the invention preferably comprises approximately 1 to approximately 99% by weight, furthermore preferably approximately 2 to approximately 98% by weight, of at least one 2-alkylisothiazolin-3-one or at least one derivative thereof or a mixture of at least one 2-alkylisothiazolin-3-one and at least one derivative thereof (component a)).

2-Alkylisothiazolin-3-ones which can be employed for the purpose of the invention have an octanol/water partition coefficient (logPow) of from approximately 3 to approximately 5. However, the logPow can adopt any values within these limits, such as, for example, about 3.2, about 3.5, about 3.9, about 4.1, about 4.5, about 4.7 or about 4.9.

The substances defined in this manner include, for example, the compounds 2-n-nonyl-, 2-n-decyl-, 2-n-undecyl-, 2-(2,5,5-trimethyl)hexyl-, 2-(3,5,5-trimethyl)hexyl-, 2-(2-methyl)octyl-, 2-(8-methyl)nonyl-, 2-(5,7-dimethyl)octyl-, 2-(3,5,7-trimethyl)heptyl- and 2-(2,8-dimethyl)nonylisothiazolin-3-one which may be branched or straight-chain in the alkyl chain.

Here, particular preference is given to 2-n-nonylisothiazolin-3-one and 2-n-decyl-isothiazolin-3-one.

The component a) may comprise the abovementioned compounds on their own, or as a mixture of two or more of these. If appropriate, the component a) may comprise other 2-alkylisothiazolin-3-ones, such as, for example, 2-n-octylisothiazolin-3-one, 4,5-dichloro-2-octylisothiazolin-3-one or 2-n-dodecylisothiazolin-3-one, which have a logPow different from 3 to 5. However, the proportion of such 2-alkylisothiazolin-3-ones in the component a) should be less than 50% by weight, preferably less than 40% by weight and particularly preferably less than 30% by weight, based on the overall weight of the active substance.

The addition of such other 2-alkylisothiazolin-3-ones, which do have very good activity but which are leached out relatively quickly, may serve, for example, to offer particularly good protection in the initial phase of an application.

The abovementioned 2-alkylisothiazolin-3-ones can be prepared, for example, as in U.S. Pat. No. 4,243,403 (in particular as described therein in column 3, line 48 to column 6, line 33, or in the examples).

In addition to the component a), the mixtures according to the invention comprise another microbiocidaly active, preferably algicidally active, component b) which differs from component a).

Suitable components b) for use in the mixtures according to the invention are, for example, benzimidazol-2-yl methylcarbamate, thiabendazole, 2-thiocyanatomethyl-thiobenzothiazole, iodopropargyl butylcarbamate, methylene bisthiocyanate, zinc pyrithione, silver salts, tebuconazole, propiconazole, folpet, tetrachlorodicyanobenzene or imazalil or mixtures of two or more of these.

However, the component b) preferably contains exclusively, or at least in addition to other microbiocidaly active compounds, such as, for example, those mentioned above, at least one triazine or one urea derivative or a mixture of two or more of these.

Particular preference is given to a compound or a mixture of two or more compounds of the formula I

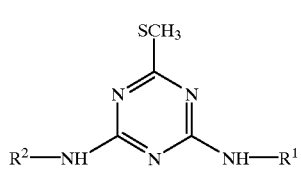

(I)

where $R^1$ and $R^2$ represent alkyl or cycloalkyl groups having 1 to 12 carbon atoms, preferably represent ethyl, tert-butyl and/or cyclopropyl or a compound or a mixture of two or more compounds of the formula II

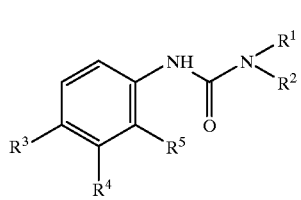

(II)

where $R^1$ and $R^2$, in each case independently of one another, represent linear or branched alkyl groups having 1 to 12 carbon atoms, preferably represent methyl, $R^3$ and $R^4$, in each case independently of one another, represent chlorine, bromine, alkyl, trifluoromethyl or O-aryl, where the aryl may optionally be substituted by alkyl groups having up to 24 carbon atoms or by alkoxy groups having up to 12 carbon atoms, and $R^5$ represents hydrogen, chlorine, bromine, fluorine or a linear or branched alkyl radical having 1 to 12 carbon atoms, or a mixture of two or more of the above compounds of the general formulae (I) and (II).

Preferred components b) are commercially available triazine and/or urea derivatives, such as, for example, ametryn, desmetryn, dimethametryn, dipropetryn, methoprotryn, prometryn, terbutryn, 2-methylthio-4-cyclopropylamino-6-t-butylamino-1,3,5-triazine (Mctt), chlorbromuron, chlortoluron, diuron, difenoxuron, fluormeturon, isoproturon or neburon or mixtures of two or more of these. Particular preference is given to 2-methylthio-4-cyclopropylamino-6-t-butylamino-1,3,5-triazine (Mctt).

If the component b) comprises mixtures of triazine and/or urea derivatives and other microbiocidaly active compounds which do not belong to the triazine or urea derivatives nor to the compounds of component a), the component b) preferably contains a proportion of at least approximately 1% by weight, particularly preferably a proportion of at least approximately 10% by weight, in each case based on the overall weight of the active substance, of the triazine and/or urea derivatives, the upper limit of the triazine and/or urea derivative content being 90% by weight, in particular for economical reasons.

The microbiocidal mixtures preferably comprise a proportion of in each case from 20 to 80% by weight of the components a) and b), the sum of a) and b) in each case being 100% by weight of the active substance of the mixture.

In general, the ratio by weight of the component a) to the component b) is from approximately 1:10 to approximately 10:1, preference being given to a ratio by weight of from approximately 1:5 to approximately 5:1.

In general, the mixtures according to the invention are formulated with additives, such as solvents, emulsifiers, stabilizers, antioxidants and the like, for example for better release or to facilitate application in a particular form. Such mixtures which, in addition to the active substance, comprise other compounds which are not microbiocidaly active in comparison to component a) and component b), at an identical use concentration, are referred to as "preservatives" in the context of the present text.

The invention accordingly also provides preservatives comprising from 1 to 99% by weight of a mixture of components a) and b) as defined in the context of this text, and from 1 to 99% by weight of at least one component selected from the group consisting of
  i) formulation auxiliaries
  ii) solvents
  iii) surfactants (emulsifiers, dispersants)
  iv) protective colloids
  v) UV stabilizers
  vi) defoamers
  vii) fillers
  viii) pigments.

The formulation auxiliaries i) include, for example, thickeners.

The mixtures according to the invention can be dissolved both in organic, essentially polar or nonpolar solvents (ii) or in mixtures of such solvents and be provided for later use. Such preservatives are then generally employed in the production of plastics, in the production of solvent-containing coating materials or for the microbiocidal finishing of other materials which may be exposed to weathering, such as, for example, leather, sealants, wood, textiles and adhesives. Suitable solvents (ii) are, for example, glycols, such as ethylene glycol, propylene glycol, butylene glycol, or glycol ethers, such as di- or polyethylene glycol, or the corresponding higher glycol ethers, such as, for example, di- or polybutylene glycol. The glycols and glycol ethers may be capped at one or at both terminal OH groups with an alkyl group, preferably a methyl group. Also suitable is the use of less polar solvents, such as, for example, tetrahydrofuran, dioxane, alkyl esters of low-molecular-weight carboxylic acids with short-chain monobasic alcohols, such as, for example, ethyl acetate, or aliphatic or aromatic solvents, such as, for example, n-alkanes, such as n-hexane, cycloalkanes, such as cyclohexane, aromatics, such as toluene and xylene, where, depending on the area of use, the optimum solvent has to be selected depending on the hydrophilicity of the substrate.

A preservative according to the invention comprises, for example,
  (I) 2–10% by weight of 2-n-nonylisothiazolin-3-one,
  (II) 3–10% by weight of 2-methylthio-4-cyclopropylamino-6-tert-butylamino-1,3,5-triazine (Mctt) and
  (III) 80–95% by weight of butyl glycol.

The mixtures according to the invention can also be prepared as aqueous dispersions or emulsions. To this end, the mixture according to the invention is stirred into water together with a surfactant (emulsifier or dispersant) (iii) which, depending on the area of use, can be of anionic, cationic or nonionic nature, or, if appropriate, with a mixture of two or more surfactants, if appropriate together with other additives. Here, the order of the addition of the individual components is immaterial.

Suitable surfactants (iii) are the anionic surfactants which are customarily used for preparing dispersions, such as, for example, the alkali metal salts of the fatty alcohol sulphates, such as, for example, sodium lauryl sulphate, or aromatic sulphonic acids, such as, for example, the alkali metal salts of the toluenesulphonic acids. It is also possible to use nonionic surfactants, such as, for example, nonylphenol ethoxylates. For paints, cationic surfactants should not be used, because of the known compatibility problems.

A review of the surfactants (dispersants/emulsifiers) which are useful for the purpose of the invention is given, for example, in Römpp Chemie Lexikon, 9th edition, pp. 1156 to 1158, and in the standard works of organic or, specifically, surfactant chemistry known to the person skilled in the art.

It is additionally possible to add customary protective colloids (iv), such as, for example, polyvinyl alcohol or polyvinylpyrrolidone, to obtain a dispersion which is stable for a particularly long period of time.

As UV stabilizers (v), the preservatives may comprise, for example, commercial products, such as, for example, Tinuvin (Ciba-Geigy), Sanduvor (Sandoz) and Oxybenzone(2-hydroxy-4-methoxybenzophenone, HMB) (Riedel-de Haen).

Suitable defoamers (vi) for use in the preservatives according to the invention are, for example, commercial products, such as, for example, Defoamer WO 150 (Worlee-Chemie), Entschäumer FN (Hoechst AG), AGITAN 280 (Nopco-Münzing) and NOPCO 8034 E (Nopco-Münzing).

Suitable fillers (vii) or pigments (viii) for use in the preservatives according to the invention are, for example, commercial products, such as, for example, china clay (aluminium silicates), kaolin, calcium carbonate (chalk, natural or precipitated), such as, for example, OMYACARB 130 (Omya), titanium dioxide, for example TIOXYDE TR 92 (Tioxyde Group PLC), Lithopone (Sachtleben), cellulose derivatives, such as, for example, Tylose H 300 (Hoechst AG), xanthan derivatives, for example Kelzan S (Kelco), and modified sheet silicates, such as, for example, Bentone (Südchemie).

The preservatives prepared in this manner comprise the compounds of component a) in an amount of from approximately 1 to approximately 99% by weight, preferably in an amount of from approximately 1 to approximately 50% by weight and particularly preferably in an amount of from approximately 2.5 to approximately 25% by weight, depending on the desired use. Component b) is preferably present in an amount of from approximately 1 to approximately 99% by weight, preferably in an amount of from approximately 1 to approximately 50% by weight and particularly preferably in an amount of from approximately 2.5 to approximately 30% by weight.

The mixtures according to the invention have high activity and a wide activity spectrum against algae, such as, for example, Chlorella fusca, and cyano bacteria, such as, for example, Nostoc commune. Even particularly resistant algae which are insensitive towards the microbiocides which are usually employed are covered by the mixtures according to the invention.

Accordingly, the present invention also relates to the use of a mixture according to the invention or a preservative comprising the mixture according to the invention, as defined above, for the microbiocidal finishing of a plastic, of leather, paper, wood, a sealant or a coating material, preferably an aqueous coating material, such as, for example, a paint.

Furthermore, the invention relates to materials or objects, such as, for example, a plastic, for example PVC, polyurethane, polyisobutylene, leather, paper, wood, a sealant or a coating material, preferably an aqueous coating material, for example a paint, in particular a paint for wood or a mineral substrate, such as, for example, concrete or stone, comprising one of the mixtures according to the invention or one of the preservatives according to the invention as defined in the context of this text.

The objects or materials described above, preferably the coating materials, generally comprise from approximately 0.001 to approximately 5% by weight, preferably from approximately 0.005 to approximately 3% by weight, of the mixture defined above.

The term "coating material", as used in the context of the present application, relates both to coating materials as materials for coatings, such as, for example, paints and materials for plasters, and to the finished coatings per se, such as, for example, paints and plasters on buildings.

Materials comprising one of the mixtures according to the invention or one of the preservatives according to the invention furthermore have a high, long-term resistance against a large number of yeasts, such as, for example, *Candida albicans, Torula utilis, Saccharomyces cerevisiae,* mould fungi, such as, for example, *Cladosporum resinae,* Fusarium spec., Mucor spec., Alternaria spec., Ulocladium spec., *Penicillium funiculosum, Chaetomium globosum, Trichoderma viride, Sclerophoma pityophila* and timber-blueing and -discolouring fungi, such as, for example, *Aureobasidium pullulans.*

The preservatives and mixtures according to the invention are highly suitable for use in the preparation of sealants or coating materials based on solvents or water. Owing to their advantageous properties with respect to the incorporation of the microbiocidaly active compound or the mixture of microbiocidaly active compounds into the sealant or the coating material, these can be formulated in such a way that the microbiocides do not contribute to the emission of volatile organic compounds (VOC). Surprisingly, the preservatives and mixtures according to the invention and used according to the invention do not significantly change the mechanical properties or the seal of coating, if at all.

The use concentration of the preservatives or mixtures according to the invention in the objects finished with them, in particular in the sealants or coating materials, is generally such that the concentration of microbiocidaly active compound is from approximately 0.001 to approximately 5% by weight, preferably from approximately 0.005 to approximately 3% by weight and particularly preferably from approximately 0.05 to approximately 1% by weight, in each case based on the total weight of the object, in particular based on the sealant or the coating material.

Coating materials which are suitable for being finished according to the invention are all coating materials which are customary in the coating industry. These are, in particular, polystyrene resins, vinyl ester resins, such as, for example, vinyl acetate resins, polybutadiene resins, acrylonitrile-butadiene-styrene copolymers, alkyd resins, polyacrylate resins, melamin-formaldehyde condensates.

Aqueous polymer dispersions, such as, for example, those based on acrylates, styrene acrylates, vinyl esters and their copolymers, serve, for example, as binders in paints and plasters. In addition to the binder, there are therefore other functional components present in the coating materials. Particular mention may be made of pigments, fillers, auxiliaries, such as, for example, film-formers, defoamers, UV stabilizers and hydrophobic agents. An example of an advantageous coating material which is highly suitable for exterior applications is MOWILITH® DM 771 from Hoechst AG.

If appropriate, the preservative according to the invention can be formulated in such a way that it already comprises one or more of the functional components intended for the coating material. If appropriate, this may be one of the components or a mixture of a plurality of the components listed in this text under i) to ix).

The abovementioned coating materials are prepared by mixing a preservative or mixture according to the invention with the appropriate coating material which is to be provided with a microbiocidal finish.

The mixtures according to the invention may be incorporated into or applied to the object, preferably the sealant or the coating material, either in pure form or as preservative, as mentioned above.

The invention furthermore relates to the use of at least one 2-alkylisothiazolin-3-one or at least one derivative thereof or a mixture of at least one 2-alkylisothiazolin-3-one and at least one derivative thereof, where the at least one 2-alkylisothiazolin-3-one or the at least one derivative thereof has an octanol/water partition coefficient (logPow) of from 3 to 5, for preventing the growth of photoautotrophic microorganisms and for preventing the growth of fungi of the order Alternaria, Mucor or Ulocladium and also of yeasts, preferably in each case in a plastic, in leather, paper, wood, a sealant or a coating material, preferably an aqueous coating material.

The examples below serve to illustrate the invention. Unless stated otherwise, stated amounts such as per cent or parts are in each case to be understood as per cent by weight or parts by weight and are based on the weight of the total formulation.

EXAMPLES

Example 1

The octanol/water partition coefficients were determined from the retention times on an RP 18 chromatography column using the HPLC method in accordance with OECD guideline 117. Bisalkylphthalates (*Handbook of Environmental Fate and Exposure Data,* Vol. 1, 1989) were used as comparative substances with a known octanol/water partition coefficient.

TABLE 1

Determination of the octanol/water partition coefficients (logPow)

| Number of carbon atoms in the 2-n-alkyl radical | logPow | Remarks |
|---|---|---|
| 8 | 2.89 | comparison |
| 9 | 3.51 | |
| 10 | 4.14 | |
| 11 | 4.76 | |
| 12 | 5.36 | comparison |

Example 2
Determination of the Relative Leaching Rate From House Paint

First, 128 parts by weight (PW) of water were initially charged. 11 PW of a 10% strength by weight solution of Calgon N (sodium triphosphate) were subsequently stirred into the water. Thereafter, 2 PW of Tylose MHB 6000 (from Hoechst AG), 3 PW of Additol XW 330 (from Hoechst AG), 4 PW of Agitan 260 (from Münzing-Chemie, Heilbronn), 226 PW of titanium dioxide (for example from Kronos 2065), 375 PW of MOWILITH® DM 771 (about 50%) (from. HOECHST), 84 PW of Omyacarb 5 (from Omya), 84 PW of Micro Mica W1, 38 PW of Micro Talc AT 1 and 20 PW of China Clay D were added and homogenized. 11 PW of white spirit, 8 PW of butyl diglycol acetate and 4 PW of MERGAL® K 9 N (Riedel de Haën) were stirred into the resulting mixture. The pH of the resulting house paint was 8.8.

The preservatives listed in Table 2 were homogeneously dispersed into the resulting house paint.

TABLE 2

| Fungicide | c [mg/kg] | |
|---|---|---|
| 2-n-nonylisothiazolin-3-one (NITZ) | 130 | |
| 2-n-decyclisothiazolin-3-one (DITZ) | 160 | |
| 2-n-octylisothiazolin-3-one (OITZ) | 250 | comparison |
| Mctt | 100 | algicide-internal standard |

The resulting paint sample was in each case drawn out to a film of approximately 150 g/m$^2$ on paper, using a knife. The paint sample prepared in this manner was subsequently dried at a temperature of 30° C. for 72 hours.

Test samples having a diameter of 5.5 cm were punched out from the paint sample. To simulate leaching by rainwater, these paint-coated test samples were watered with tap water (46.7 l/day/m$^2$ of paint). Test samples were taken in each case after 24 hours and air-dried for 72 hours.

To determine the microbicide concentration, in each case one specimen was extracted in methanol. The methanol extracts were analysed by HPLC.

HPLC conditions:
    column: RP-phenyl (Hypersil 5 μ)
    mobile phase: gradient water/acetonitrile
    UV-Detector: 220 nm and 200 nm Since in each analysis, the substances listed in Table 3 were measured as the area under the HPLC signal, it is possible to relate the leaching rates directly to the known active compounds OITZ and Mctt.

TABLE 3

| | HPLC area (in arbitrary units) (relative area in brackets) | | | | residual concentration, relative to the residual concentration of Mctt | | |
|---|---|---|---|---|---|---|---|
| [h] | Mctt | OITZ | NITZ | DITZ | OITZ (Comparison) | NITZ | DITZ |
| 0 | 955.2 (1) | 2,170.8 (1) | 1,015.6 (1) | 1,226.1 (1) | 1.000 | 1.000 | 1.000 |
| 24 | 787.1 (0.824) | 555.1 (0.25) | 647.7 (0.637) | 1,087.9 (0.886) | 0.310 | 0.774 | 1.077 |
| 48 | 800.2 (0.837) | 273.0 (0.126) | 539.3 (0.531) | 1,094.1 (0.892) | 0.150 | 0.634 | 1.065 |
| 72 | 677.6 (0.708) | 64.0 (0.029) | 327.8 (0.322) | 897.1 (0.731) | 0.042 | 0.455 | 1.032 |
| 96 | 547.4 (0.572) | 8.1 (0.004) | 151.3 (0.149) | 645.7 (0.526) | 0.007 | 0.260 | 0.919 |

After watering for 96 hours, the residual concentration of the known OITZ is only 0.7% of the Mctt concentration which had been employed at the same time. After a corresponding period of exposure to the weather, the fungicide/algicide ratio is no longer suitable for a comprehensive preservation of the film.

For the compounds NITZ and DITZ according to the invention, the leaching characteristic is considerably better balanced. The concentration after 96 hours is 26% and 91.9%, respectively, of the residual Mctt concentration. Even after stress by leaching, the fungicide/algicide ratio is therefore still suitable for a comprehensive preservation of the film.

Example 3
Determination of the Long-Term Protection of a House Paint Against Colonization by Fungi Similarly to Example 1, fungicides were stirred, in accordance with Example 1, into samples of a house paint, paint samples were prepared and watered. To test the protection against colonization by fungi, the paint samples which had been prepared in this manner were sterilized under UV light and applied to nutrient media for fungi in Petri dishes which had been inoculated beforehand with a spore mixture of the test fungi *Aspergillus niger* and *Penicilium funiculosum*. The Petri dishes were then stored at 29° C. in a heating cabinet at 80% relative atmospheric humidity for 7 days. The growth of the test fungi on the sample paints and the nutrient medium was then evaluated using the following scheme:

| | |
|---|---|
| 0H | test sample not colonized, inhibitory zone on the nutrient medium |
| 0 | test sample not colonized |
| 1 | test sample slightly colonized, less than 10% of the surface |
| 2 | test sample colonized, 10 to 30% of the surface |
| 3 | test sample colonized to a considerable extent, 30 to 60% of the surface |
| 4 | test sample colonized strongly, more than 60% of the surface |

TABLE 4

| | | colonization by fungi | | | | |
|---|---|---|---|---|---|---|
| Paint No. | Fungicide | Initial concentration of the fungicide in the paint [mg/kg] | without watering | 48 h of watering | 96 h of watering | Remarks |
| 1 | none | — | 4 | 4 | 4 | blank sample |
| 2 | dodecyl-ITZ | 1660 | 2 | 4 | 4 | comparison |

TABLE 4-continued colonization by fungi

| Paint No. | Fungicide | Initial concentration of the fungicide in the paint [mg/kg] | without watering | 48 h of watering | 96 h of watering | Remarks |
|---|---|---|---|---|---|---|
| 3 | DITZ | 1000 | 0 | 1 | 1 | |
| 4 | NITZ | 765 | 0H | 0 | 2 | |
| 5 | OITZ | 1500 | 0H | 1 | 4 | comparison |

Evaluation

If there is no stress caused by the weather, the paint finished with the comparative product OITZ is protected well against colonization by fungi. However, after watering for 96 h, this protection is lost completely. In contrast, the comparative product dodecyl-ITZ is not sufficiently active in the paint, even when it is not exposed to the weather.

Even after exposure to the weather, the active compounds NITZ and DITZ according to the invention keep the paint surface predominantly free from colonization. The fungicidal protection is only reduced to a small extent on exposure to the weather.

Example 4
Determination of the Long-Term Protection of a House Paint Against Colonization by *Ulocladium consortiale*

The method of Example 3 was used.

TABLE 5

Long-term protection against Ulocladium consortiale

| Paint No. | Fungicide | Initial concentration of the fungicide in the paint [mg/kg] | without watering | 48 h of watering | 96 h of watering | Remarks |
|---|---|---|---|---|---|---|
| 1 | none | — | 4 | 4 | 4 | blank sample |
| 2 | dodecyl-ITZ | 1660 | 1 | 4 | 4 | comparison |
| 3 | DITZ | 1000 | 0 | 1 | 2 | |
| 4 | NITZ | 765 | 0H | 0 | 2 | |
| 5 | OITZ | 1500 | 0H | 0 | 4 | comparison |

Example 5
Examination of the Algistatic Preservation of Films 0.025% of DITZ and 0.025% of finely ground Mctt were incorporated into a microbicide-free commercial filler paint for houses which was based on an acrylate dispersion.

For comparison, one in each case similar paint sample was finished with 0.025% of Mctt and OITZ, respectively, in accordance with the prior art.

The paint samples obtained in this manner were applied, in each case at 300 g/m², to filter paper discs (No. 597 from Schleicher & Schüll, diameter 5.5 cm) and subsequently dried at a temperature of 30° C. for 72 hours.

To simulate leaching by rainwater, the paint-coated test samples were watered with tap water for 96 hours. The leaching water was changed in each case after 24 hours.

The examination of the resistance to colonization by algae was carried out on solid Bold algae nutrient media. The dry test samples were, after sterilization of both sides under UV light, applied to the nutrient media in Petri dishes. Under sterile conditions, the surface to be examined was inoculated with in each case 5 ml of a well-grown algae culture in Bold nutrient solution, so that the surface of the paint was coloured light-green.

After a cultivation time of 14 days at a temperature of 22° C., the degree of colonization by algae on the paints was assessed visually using a scale from 0 to 4:

| | |
|---|---|
| 0 | paint not colonized |
| 1 | paint slightly colonized, less than 10% of the surface |
| 2 | paint colonized, 10 to 30% of the surface |
| 3 | paint colonized, 30 to 60% of the surface |
| 4 | paint overgrown, more than 60% of the surface |

TABLE 6

Examination of the algistatic preservation of films

| Preservative | Concentration | Colonization by Chlorella fusa | |
|---|---|---|---|
| DITZ + Mctt | 0.025% + 0.025% | 0 | |
| OITZ + Mctt | 0.025% + 0.025% | 1 | comparison |

What is claimed is:

1. A biocidal composition comprising, as biocidally active components, a mixture consisting essentially of at least one biocidally active 2-alkylisothiazolin-3-one and at least one other biocidally active component wherein there is present at least one 2-alkylisothiazolin-3-one having an octanol/water partition coefficient (log Pow) of from 3 to 5.

2. The biocidal composition of claim 1 wherein the 2-alkylisothiazolin-3-one is taken from the group consisting of 2-n-nonylisothiazolin-3-one, 2-n-decylisothiazolin-3-one, 2-n-undecylisothiazolin-3-one, 2-(2,5,5-trimethyl)-hexylisothiazolin-3-one, 2-(3,5,5-trimethyl)hexylisothiazolin-3-one, 2-(2-methyl)octylisothiazolin-3-one, 2-(8-methyl)nonylisothiazolin-3-one, 2-(5,7-dimethyl)octylisothiazolin-3-one, 2-(3,5,7-trimethyl)heptylisothiazolin-3-one and 2-(2,8-dimethyl)nonylisothiozolin-3-one.

3. The biocidal composition of claim 2 wherein there is present a biocidally active component chosen from the group consisting of a triazine of the formula

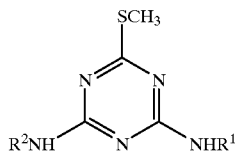

wherein $R^1$ and $R^2$ of the triazine may be the same or different and are selected from the group consisting of alkyl and cycloalkyl groups having 1 to 12 carbon atoms and a urea of the formula

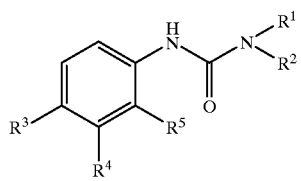

wherein $R^1$ and $R^2$ of the urea may be the same or different and are chosen from the group consisting of linear or branched alkyl groups having from 1 to 12 carbon atoms; wherein R³ and R⁴ may be alike or different and are chosen from the group consisting of chlorine, bromine, alkyl, trifluoromethyl and O-aryl wherein the aryl group may be substituted with one or more alkyl groups having up to a total of 24 carbon atoms and wherein R⁵ represents hydrogen, chlorine, bromine, fluorine or a linear or branched alkyl radial having from 1 to 12 carbon atoms.

4. The biocidal composition of claim 3 which includes at least one of the ingredients selected from the group consisting of formulation auxiliaries, solvents, surfactants, protective colloids, UV stabilizers, defoamers, fillers and pigments.

5. The biocidal composition of claim 3 wherein R¹ and R² of the triazine are selected from the group consisting of ethyl, tertiarybutyl and cyclopropyl and R¹ and R² of the urea are both methyl.

6. The biocidal composition of claim 5 which includes at least one of the ingredients selected from the group consisting of formulation auxiliaries, solvents, surfactants, protective colloids, UV stabilizers, defoamers, fillers and pigments.

7. The biodical composition of claim 5 wherein the 2-alkylisothiazolin-3-one is 2-n-nonylisothiazolin-3-one or 2-n-decylisothiazolin-3-one and the triazine is 2-methylthio-4-cyclopropylamino-6-tertiarybutylamino-1,3,5-triazine.

8. The biocidal composition of claim 7 containing:
   a) 2–10% by weight of 2-n-nonylisothiazolin-3-one
   b) 3–10% by weight of 2-methylthio-4-cyclopropylamino-6-tertiarybutylamino-1,3,5-triazine, and
   c) 80–95% by weight of butyl glycol.

9. A method for protecting a substrate from microbial infestation which comprises treating said substrate with an effective amount of a biocidal composition which has, as biocidally active components,
   a) a 2-alkylisothiazolin-3-one which is taken from the group consisting of 2-n-nonylisothiazolin-3-one, 2-n-decylisothiazolin-3-one, 2-n-undecylisothiazolin-3-one, 2-(2,5,5-trimethyl)-hexylisothiazolin-3-one, 2-(3,5,5-trimethyl)hexylisothiazolin-3-one, 2-(2-methyl)octylisothiazolin-3-one, 2-(8-methyl)nonylisothiazolin-3-one, 2-(5,7-dimethyl)octylisothiazolin-3-one, 2-(3,5,7-trimethyl)heptylisothiazolin-3-one and 2-(2,8-dimethyl)nonylisothiozolin-3-one, and
   b) at least one other biocidally active component chosen from the group consisting of a triazine of the formula

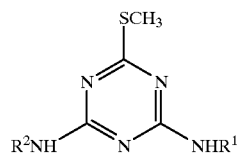

wherein R¹ and R² of the triazine may be the same or different and are selected from the group consisting of alkyl and cycloalkyl groups having 1 to 12 carbon atoms and a urea of the formula

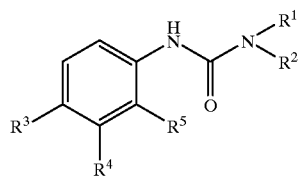

wherein R¹ and R² of the urea may be the same or different and are chosen from the group consisting of linear or branched alkyl groups having from 1 to 12 carbon atoms; wherein R³ and R⁴ may be alike or different and are chosen from the group consisting of chlorine, bromine, alkyl, trifluoromethyl and O-aryl wherein the aryl group may be substituted with one or more alkyl groups having up to a total of 24 carbon atoms; and wherein R⁵ represents hydrogen, chlorine, bromine, fluorine or a linear or branched alkyl radial having from 1 to 12 carbon atoms
wherein there is present at least one 2-alkylisothiazolin-3-one having an octanol/water partition coefficient (log Pow) of from 3 to 5.

10. The method of claim 9 to wherein the biocidal composition includes at least one of the ingredients selected from the group consisting of formulation auxiliaries, solvents, surfactants, protective colloids, UV stabilizers, defoamers, fillers and pigments.

11. The method of claim 9 wherein R¹ and R² of the triazine are selected from the group consisting of ethyl, tertiarybutyl and cyclopropyl and R¹ and R² of the urea are both methyl.

12. The method of claim 11 wherein the 2-alkylisothiazolin-3-one is selected from the group consisting of 2-n-nonylisothiazolin-3-one and 2-n-decylisothiazolin-3-one and the triazine is 2-methylthio4-cyclopropylamino-6-tertiarybutylamino-1,3,5-triazine.

13. The method of claim 12 to wherein the biocidal composition includes at least one of the ingredients selected from the group consisting of formulation auxiliaries, solvents, surfactants, protective colloids, UV stabilizers, defoamers, fillers and pigments.

14. The method of claim 13 wherein the biocidal composition contains,
   a) 2–10% by weight of 2-n-nonylisothiazolin-3-one
   b) 3–10% by weight of 2-methylthio-4-cyclopropylamino-6-tertiarybutylamino-1,3,5-triazine, and
   c) 80–95% by weight of butyl glycol.

15. A coating composition comprising an effective amount of a biocidal composition which has, as biocidally active components,
   a) a 2-alkylisothiazolin-3-one which is taken from the group consisting of 2-n-nonylisothiazolin-3-one, 2-n-decylisothiazolin-3-one, 2-n-undecylisothiazolin-3-one, 2-(2,5,5-trimethyl)-hexylisothiazolin-3-one, 2-(3,5,5-trimethyl)hexylisothiazolin-3-one, 2-(2-methyl)octylisothiazolin-3-one, 2-(8-methyl)nonylisothiazolin-3-one, 2-(5,7-dimethyl)octylisothiazolin-3-one, 2-(3,5,7-trimethyl)heptylisothiazolin-3-one and 2-(2,8-dimethyl)nonylisothiozolin-3-one, and
   b) at least one other biocidally active component chosen from the group consisting of a triazine of the formula

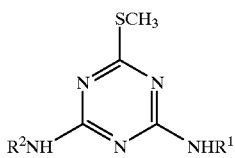

wherein R¹ and R² of the triazine may be the same or different and are selected from the group consisting of alkyl and cycloalkyl groups having 1 to 12 carbon atoms and a urea of the formula

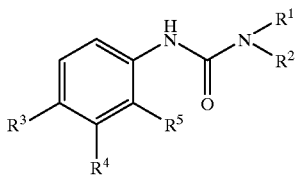

wherein R¹ and R² of the urea may be the same or different and are chosen from the group consisting of linear or branched alkyl groups having from 1 to 12 carbon atoms; wherein R³ and R⁴ may be alike or different and are chosen from the group consisting of chlorine, bromine, alkyl, trifluoromethyl and O-aryl wherein the aryl group may be substituted with one or more alkyl groups having up to a total of 24 carbon atoms, and wherein R⁵ represents hydrogen, chlorine, bromine, fluorine or a linear or branched alkyl radial having from 1 to 12 carbon atoms wherein there is present at least one 2-alkylisothiazolin-3-one having an octanol/water partition coefficient (log Pow) of from 3 to 5.

16. The coating composition of claim 15 wherein the biocidal composition also includes at least one of the ingredients selected from the group consisting of formulation auxiliaries, solvents, surfactants, protective colloids, UV stabilizers, defoamers, fillers and pigments.

17. The coating composition of claim 16 wherein R¹ and R² of the triazine are selected from the group consisting of ethyl, tertiarybutyl and cyclopropyl and R¹ and R² of the urea are both methyl.

18. The coating composition of claim 17 wherein the 2-alkylisothiazolin-3-one is selected from the group consisting of 2-n-nonylisothiazolin-3-one and 2-n-decylisothiazolin-3-one and the triazine is 2-methylthio-4-cyclopropylamino-6-tertiarybutylamino-1,3,5-triazine.

19. The coating composition of claim 18 wherein the biocidal composition also includes at least one of the ingredients selected from the group consisting of formulation auxiliaries, solvents, surfactants, protective colloids, UV stabilizers, defoamers, fillers and pigments.

20. The coating composition of claim 19 wherein the biocidal composition includes a) 2–10% by weight of 2-n-nonylisothiazolin-3-one b) 3–10% by weight of 2-methylthio-4-cyclopropylamino-6tertiarybutylamino-1,3,5-triazine, and c) 80–95% by weight of butyl glycol.

* * * * *